United States Patent
Clauson et al.

(10) Patent No.: US 10,154,924 B2
(45) Date of Patent: Dec. 18, 2018

(54) SCHLEMM'S CANAL DEVICES AND METHOD FOR IMPROVING FLUID FLOW

(71) Applicant: Novartis AG, Basel (CH)

(72) Inventors: Luke Clauson, Menlo Park, CA (US); Michael Schaller, Menlo Park, CA (US)

(73) Assignee: Novartis AG, Basel (CH)

( * ) Notice: Subject to any disclaimer, the term of this patent is extended or adjusted under 35 U.S.C. 154(b) by 368 days.

(21) Appl. No.: 14/163,364

(22) Filed: Jan. 24, 2014

(65) Prior Publication Data

US 2014/0213958 A1    Jul. 31, 2014

Related U.S. Application Data

(60) Provisional application No. 61/757,603, filed on Jan. 28, 2013.

(51) Int. Cl.
*A61F 9/007* (2006.01)

(52) U.S. Cl.
CPC .................... *A61F 9/00781* (2013.01)

(58) Field of Classification Search
CPC .................................................. A61F 9/00781
See application file for complete search history.

(56) References Cited

U.S. PATENT DOCUMENTS

| 5,180,362 A | 1/1993 | Worst |
| 2009/0182421 A1* | 7/2009 | Silvestrini ........... A61F 9/00781 623/6.13 |
| 2011/0196487 A1* | 8/2011 | Badawi ............... A61F 9/00781 623/4.1 |
| 2012/0323159 A1* | 12/2012 | Wardle ................ A61F 9/00781 604/8 |

* cited by examiner

*Primary Examiner* — Tatyana Zalukaeva
*Assistant Examiner* — Kai Weng
(74) *Attorney, Agent, or Firm* — Mintz Levin Cohn Ferris Glovsky and Popeo, P.C.

(57) ABSTRACT

This disclosure relates generally to methods and devices for an ocular implant which can be positioned in the Schlemm's canal of a patient's eye for improving fluid flow, such as aqueous fluid, through the eye. The ocular implant can have a variety of shapes and sizes which can allow the ocular implant to be implanted in the Schlemm's canal for applying a force, including a predetermined force, along a part of the Schlemm's canal. The force applied by the ocular implant can change the shape of the Schlemm's canal which can increase the flow volume within and through the Schlemm's canal.

21 Claims, 11 Drawing Sheets

SCHLEMM'S CANAL DEVICES AND METHOD FOR IMPROVING FLUID FLOW

REFERENCE TO PRIORITY DOCUMENT

This application claims priority benefit under 35 U.S.C. § 119(e) of U.S. Provisional Patent Application Ser. No. 61/757,603, filed Jan. 28, 2013, and entitled "SCHLEMM'S CANAL IMPLANT FOR IMPROVING FLUID FLOW." The priority of the filing date is hereby claimed, and the disclosure of the provisional patent application is hereby incorporated by reference in its entirety.

BACKGROUND

This disclosure relates generally to methods and devices associated with an ocular implant for increasing aqueous flow through the Schlemm's canal of an eye which can reduce inner ocular pressure of the eye, such as for patients suffering glaucoma.

The mechanisms that cause glaucoma are not completely known. It is known that glaucoma results in abnormally high pressure in the eye which can lead to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye, such as for shunting fluid out of the anterior chamber in order to regulate pressure in the eye. In addition, some procedures have been developed in an attempt to increase the flow of aqueous fluid in the eye, such as some canaloplasty procedures. However, at least some canaloplasty procedures require the surgeon to create the necessary forces that the implant will apply in the eye in order to increase aqueous flow through the eye. For example, some canaloplasty procedures requires the surgeon to tighten and secure a suture in order to force the suture to apply a radial force on the inner wall of the Schlemm's canal and stent the Schlemm's canal open. A number of difficulties and opportunities for error arise under these types of procedures, such as due to user error.

For example, determining the appropriate amount of tension to apply on the suture in order to create the appropriate amount of radial tension along the inner wall of the Schlemm's canal can result in user error. For example, the suture can get snagged or improperly placed within the Schlemm's canal which can affect the surgeon's ability to determine an appropriate amount of tension to apply to the suture prior to securing the suture. Additionally, in some canalostomy procedures the suture may be secured with a knot and the tension applied to Schlemm's canal may reduce over time both from stretching of the suture material and slippage at the suture knot. Any number of issues can arise that can result in a suture not having an appropriate amount of tension, including too much tension, which can damage the Schlemm's canal. In addition, a suture having too much or not enough tension can result in an ineffective procedure at best and can require additional ocular surgeries to repair the faulty procedure.

In view of the foregoing, there is a need for durable ocular implant systems and methods that can improve aqueous flow through the Schlemm's canal, such as by providing an appropriate amount of radial force on the Schlemm's canal without requiring the surgeon to create or apply the force.

BRIEF DESCRIPTION OF THE DRAWINGS

These and other aspects will now be described in detail with reference to the following drawings.

Like reference symbols in the various drawings indicate like elements.

DETAILED DESCRIPTION

The disclosed ocular implant can be configured to be implanted into the Schlemm's canal for assisting in improving aqueous flow through the Schlemm's canal. The disclosed ocular implant can be configured to apply a force, including a predetermined force, along at least a part of the Schlemm's canal in order to increase the flow volume through the Schlemm's canal. An increase in aqueous flow through the Schlemm's canal can assist in improving inner ocular pressure (10P) in an eye, such as an eye suffering from Glaucoma.

Figure 1:
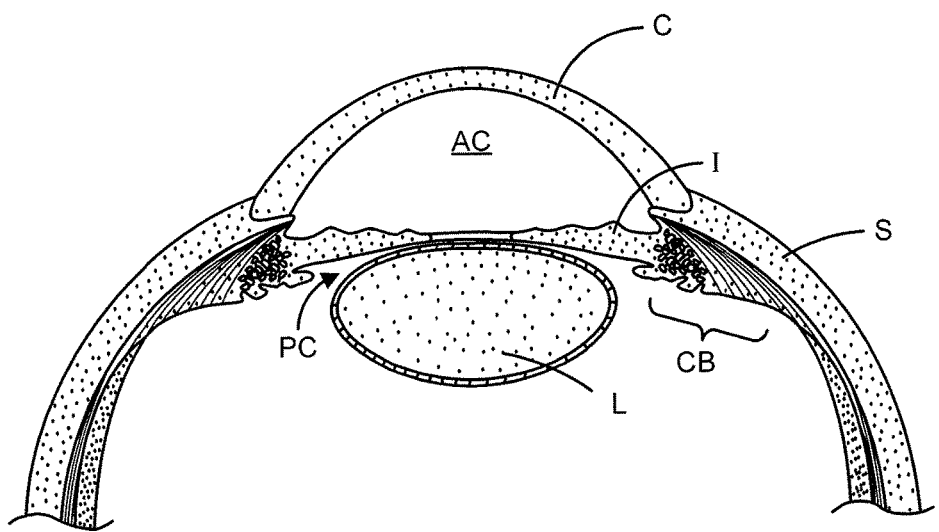
FIG. 1 shows a cross-sectional view of a portion of the human eye.

FIG. 1 shows a cross-sectional view of a portion of the human eye which is generally spherical and covered on the outside by the sclera S. The retina (not shown) lines the inside posterior half of the eye. The retina registers the light and sends signals to the brain via the optic nerve. The bulk of the eye is filled and supported by a vitreous body, which is a clear, jelly-like substance. The elastic lens L is located near the front of the eye. The lens L provides adjustment of focus and is suspended within a capsular bag from the ciliary body CB which contains the muscles that change the focal length of the lens L.

A volume in front of the lens L is divided into two by the iris I, which controls the aperture of the lens L and the amount of light striking the retina. The pupil is a hole in the center of the iris I through which light passes. The volume between the iris I and the lens L is the posterior chamber PC. The volume between the iris I and the cornea C is the anterior chamber AC. Both chambers are filled with a clear liquid known as aqueous humor. The ciliary body CB can continuously form aqueous humor in the posterior chamber PC by secretion from the blood vessels. The aqueous humor can flow around the lens L and iris I into the anterior chamber AC and exit the eye through the trabecular meshwork TM.

Figure 2:
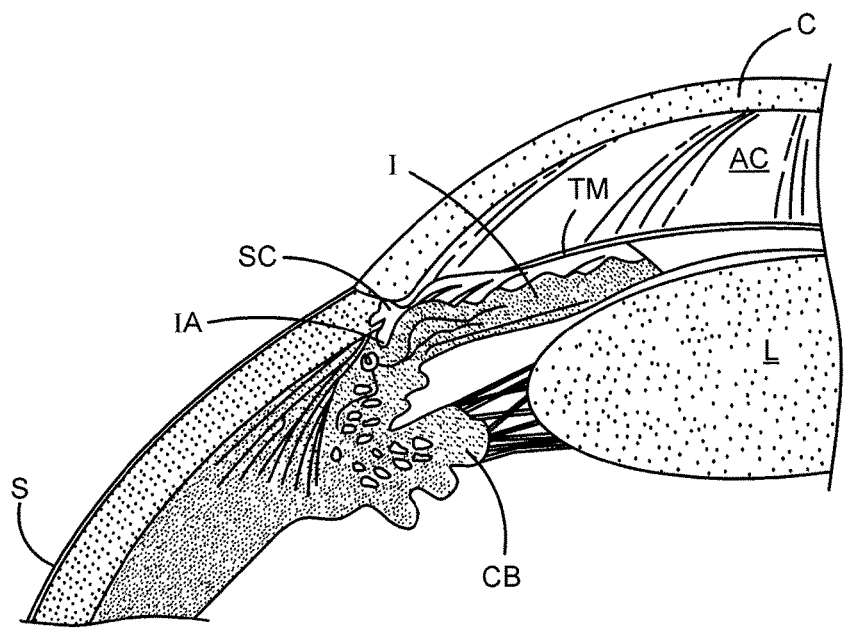
FIG. 2 is a cross-sectional view of a portion of the human eye showing the iridocorneal angle of the eye and surrounding tissue structures.

FIG. 2 is a cross-sectional view of a portion of the human eye showing the iridocorneal angle ("the angle") IA of the eye and surrounding tissue structures. A view of the angle IA can provide a variety of information to a clinician viewing the angle IA, including the health and condition of the eye. The angle IA is positioned between the iris I and the cornea C and plays an important role in the circulation of aqueous fluid in the eye.

The trabecular meshwork TM is an area of tissue in the eye located around the base of the cornea C, near the ciliary body CB, and is responsible for draining the aqueous humor from the eye via the anterior chamber AC. The trabecular meshwork TM is spongy and can allow fluid to drain into the Schlemm's canal SC. The Schlemm's canal SC, also known as canal of Schlemm or the scleral venous sinus, is a circular channel in the eye that collects aqueous humor from the anterior chamber AC and delivers it into the bloodstream via the anterior ciliary veins. The Schlemm's canal SC is essentially an endothelium-lined tube, resembling that of a lymphatic vessel. The inside of Schlemm's canal SC, nearest to the aqueous humor, is covered by the trabecular meshwork TM. This region can make the greatest contribution to outflow resistance of the aqueous humor.

The disclosed ocular implant can be a variety of shapes and sizes which can allow the ocular implant to be implanted in the Schlemm's canal for applying a force, including a predetermined force, along a part of the Schlemm's canal. The force applied by the ocular implant can change the shape of the Schlemm's canal which can increase the flow volume within and through the Schlemm's canal.

In some implementations, the ocular implant can include a non-continuous or disconnected ring which can be implanted into the Schlemm's canal. The non-continuous ring can be configured to apply a radially inward force along at least a part of an inner part of the inside wall of the Schlemm's canal. The inward force may both create a larger cross-sectional area of Schlemm's canal by pulling the inner wall away from the outer wall, while simultaneously stimulating the trabecular meshwork which is close to the inner wall of Schlemm's canal in a way that increases fluid flow. The disclosed ocular implant may be advantageous to some of these canalostomy procedures because it may have a predetermined force that it applies to the inner wall of Schlemm's canal which may not require a surgeon to set the force by tying a knot in a suture. Additionally, the disclosed ocular implant may be more durable than a suture tied with a knot. For example, suture may lose tension over time due to stretching of the suture material, typically a prolene material, or due to slippage at the knot. The disclosed ocular implant may overcome these challenges because the force applied to the Schlemm's canal is not a result of circumferential tension as in the case of suture, but rather a radial deflection of an elastic material which is more durable. Alternatively or in addition, one or more ocular implants can be configured to apply a radially outward force along at least a part of an outer part of the outer wall of the Schlemm's canal. An outward force may be advantageous for certain ocular diseases such as narrow angle glaucoma or open angle glaucoma. In this embodiment the ocular implant may increase the cross-sectional area of Schlemm's canal while moving the Schlemm's canal further outward radially. In the case of narrow angle glaucoma this may be advantageous because in narrow angle glaucoma the angle of the eye as defined by the iris and structures such as the trabecular meshwork form a narrow angle which restricts the amount of fluid which can flow through the trabecular meshwork. The disclosed ocular implant may overcome these challenges by moving the Schlemm's canal and attached structures such as the trabecular meshwork outward radially such that the angle of the eye may be increased. Furthermore, in this embodiment an outer wall of Schlemm's canal may be able to withstand a greater radial force than an inner wall of Schlemm's canal. The tissue structures which are adjacent to an outer wall of Schlemm's canal such as the sclera may be less prone to damage at higher forces than tissue structures which are adjacent to an inner wall of Schlemm's canal such as the trabecular meshwork. Therefore, a larger force may be used in an ocular implant that expands radially outward. Furthermore, a suture which is secured during some canalostomy procedures may not impart an outward radial force because the suture is secured with a circumferential tension which imparts an inward radial force. Alternatively, the disclosed ocular implant may be configured to impart both an outward and an inward radial force on Schlemm's canal. In this embodiment the ocular implant may have the advantages of both an inward radial force and an outward radial force. Additionally, the ocular implant can be configured to further impart a vertical force on the upper or lower walls of Schlemm's canal. In these embodiments, the ocular implant can further increase the cross-sectional flow of the Schlemm's canal by separating the additional upper and lower walls of Schlemm's canal.

In addition, the ocular implants can have a variety of dimensions and be made out of a variety of materials in order to apply a variety of radial forces, at least some of which can be pre-determined, along the Schlemm's canal. For example, the ocular implant can be configured such that the implant applies a pre-determined amount of radial force along at least a part of the Schlemm's canal upon implantation in order to change the shape of the Schlemm's canal and increase the flow volume through the Schlemm's canal. Therefore, the ocular implant can be used without requiring a user, such as a surgeon, to create an appropriate amount of radial force for the implant to apply once implanted in the Schlemm's canal. Instead, the surgeon can simply determine an appropriately configured ocular implant, such as an implant appropriately sized and shaped for the patient's eye, which can provide the desired amount of expansion of the Schlemm's canal.

Once the surgeon has chosen an appropriately sized and shaped implant which can apply an appropriate amount of radial force in one or more directions within the Schlemm's canal, the surgeon can implant the ocular implant and allow the implant to achieve a configuration within the Schlemm's canal based on the characteristics of the ocular implant. This can eliminate user error by the surgeon due to the surgeon applying an inappropriate amount of radial force to a part of the Schlemm's canal which can result in an ineffective procedure. The ocular implants described herein can prevent procedure complications and reduce costs associated with additional corrective procedures by providing a surgeon with an ocular implant having known characteristics which can provide a pre-determined radial force in at least one direction within the Schlemm's canal for improving flow, such as aqueous fluid, through the Schlemm's canal. Additionally, the ocular implant can impart a durable force to the Schlemm's canal which may not significantly reduce over time.

The ocular implant can be comprised of one or more of a variety of medical grade materials in order to assist the implant with at least implantation and applying a radial force along at least a part of the Schlemm's canal. For example, the ocular implant can be made out of a flexible or shape memory material, such as nitinol. Alternatively or in addition, the ocular implant can be made out of any other suitable flexible materials, such as stainless steel, Pebax, urethane, PVDF, polyimide, shape memory plastic, or the like.

In addition, the ocular implant can have any number of a variety of dimensions which can assist with minimally invasive implantation of the ocular implant as well as in order to provide an approximate amount of radial force along at least a part of the Schlemm's canal for increasing the flow volume through the Schlemm's canal. For example, the body of the ocular implant can be comprised of a wire having a diameter approximately between 0.001 inch and 0.010 inch or approximately between 0.002 inch and 0.006 inch. In addition, the wire comprising the ocular implant can be either a solid wire or a hollow tube. For example, some embodiments of the ocular implant comprised of a hollow tube can have an outer diameter approximately between 0.002 inch and 0.012 inch with an inner diameter approximately between 0.001 inch and 0.010 inch.

As discussed above, the ocular implant can have a variety of shapes and profiles. For example, the ocular implant can have an open "C" shape profile, a closed ring profile or an over-lapping ring profile, such as similar to a key ring. In addition, the material comprising the ring can include one or more openings which can allow fluid to flow through at least a part of the implant. Alternatively or in addition, the openings in the implant can be injected with a fluid, such as a viscoelastic material.

Some embodiments of the ocular implant can be shaped such that they are larger in diameter than the Schlemm's canal of a patient. Alternatively or in addition, some embodiments of the ocular implant can be shaped such that they are smaller in diameter than the Schlemm's canal of the patient. The various shapes and sizes of the ocular implant embodiments can assist in providing various radial forces to the Schlemm's canal in order to increase the flow volume through the Schlemm's canal. For example, the ocular implant can be in the shape of a circular ring with a ring diameter which is approximately 8 mm to 10 mm in diameter, or approximately 4 mm to 16 mm in diameter. In addition, the ends of the ocular implant can have a rounded tip which can assist in implantation of the implant, such as feeding the implant through the Schlemm's canal. The rounded tip can also prevent unwanted puncturing of the Schlemm's canal. Additionally, the rounded tip can have a diameter of approximately 0.008 inch to 0.020 inch. Alternatively, any number of termination geometries may exist for the ends of the implant such as a domed end, a bulbous end, a looped end, or the like.

The ocular implant can have a variety of implanted shapes and configurations, which may be the same or different than the shape or configuration the implant had prior to implantation. For example, the ocular implant can form a "C" shape when implanted in the Schlemm's canal such that the ends of the implant remain disconnected and form an open angle. The open angle formed between the ends of the implant can form an open angle of approximately 10 degrees to 30 degrees, or approximately 5 degrees to 160 degrees. Alternatively, some ocular implant can have a disconnected ring shape with the ends of the implant overlapping at least a part of the ring, similar to a key ring. In this embodiment, the overlapping sections may provide additional radial force to the Schlemm's canal due to the increased implant material and furthermore may impart a radial force along the majority of sections of the Schlemm's canal. In some embodiments, the ocular implant can have a substantially circular shape that imparts a substantially even radial force along its circumference. Alternatively, the ocular implant can have a substantially oval shape. In this implementation the ocular implant may impart inward radial forces at certain sections of the Schlemm's canal, such as at the minor axis, and simultaneously may impart an outward radial force at still other sections of the Schlemm's canal, such as at the major axis. In still other embodiments, the ocular implant may impart additional forces on the Schlemm's canal. For example, the ends of the ocular implant may exist out of plane vertically such that when constrained by Schlemm's canal they impart an additional vertical force on the upper or lower walls of Schlemm's canal. In this embodiment, the ocular implant may appear like a helix or spiral with a predetermined vertical pitch which imparts a vertical force when it is constrained to a narrower vertical width. At least either the open "C" shape or the overlapped configuration, and any number of configurations at least described herein (e.g., oscillating shape, looped shape, etc.), can provide any number of radial forces in any number of directions, including radially inward and radially outward, along at least a part of the Schlemm's canal. However, any number of a variety of shapes and sizes can be implemented in the present ocular implant for increasing the flow volume through the Schlemm's canal without departing from the scope of this disclosure.

In some embodiments, the ocular implant may exist as a single structure comprised of a single material. The radial force imparted may significantly depend on the mechanical properties of that material, such as the Modulus of Elasticity, and the amount of deflection from its original size to the constrained size as defined by the Schlemm's canal. In other embodiments, the ocular implant may be comprised of multiple sections of varying materials and stiffness. For example, a first material may impart a certain radial force along a given section of Schlemm's canal which then is connected to a second material which imparts a second radial force along a second section of Schlemm's canal and so forth. There may exist any number of materials and mechanical properties along the circumferential length of the ocular implant. Additionally, the ocular implant may be comprised of multiple disconnected pieces which each impart a predetermined radial force. For example, one piece may impart a radial force along a given section of Schlemm's canal such as a 45-180 degree section, and a second piece may impart a radial force along a second section of Schlemm's canal. Any number of pieces and angles may be configured to impart any number of forces along the circumferential walls of Schlemm's canal.

In some embodiments, the ocular implant may have a solid round cross-sectional profile such as that of a round wire. The wire profile may provide a compact method of imparting a predetermined force to the Schlemm's canal. Alternatively, the cross-sectional profile of the ocular implant may be substantially tubular with an inner lumen and an outer surface. The lumen of the implant may be configured to allow fluid and substances to flow through the lumen such as aqueous humor, visco elastic, saline or any other number of substances. Additionally, there may exist openings or channels which provide fluid communication from the inner lumen of the implant to the outer surface of the implant. In this embodiment, substances such as aqueous humor may flow through a portion of the lumen of the ocular implant and exit through an opening to the Schlemm's canal. This may be particularly advantageous if one end of the ocular implant or a portion of the ocular implant is left in the anterior chamber. Alternatively, the lumen of the ocular implant may be used to deliver fluids or substances to the eye. For example, visco elastic may be injected through the lumen of the implant during the implantation. The visco elastic substance may flow through the lumen and out the openings to the Schlemm's canal. This may further dilate the Schlemm's canal such the cross-sectional area of the Schlemm's canal may be increased. Additionally, visco elastic materials or other substances may include drugs that would be desirable to deliver to the Schlemm's canal. Still other cross-sectional profiles of the ocular implant may exist such as a flat tape, a "C" shaped profile, a "U" shaped profile, an "E" shaped profile, or any other number of cross-sectional profiles.

In at least some embodiments of the ocular implant can be placed into the Schlemm's canal through an ab-interno procedure. For example, a surgeon can use a delivery device to access the Schlemm's canal and the implant can be inserted through a needle into the Schlemm's canal. In some embodiments, the needle can exist at the distal end of the delivery device and the surgeon can visualize the trabecular meshwork and subsequently the inner wall of Schlemm's canal and can apply the needle to the Schlemm's canal to penetrate the inner wall. The needle can be configured to align the lumen of the needle with a tangency of the Schlemm's canal by being curved at a 5 to 45 degree angle such that as the implant is advanced out of the needle, it enters smoothly into Schlemm's canal. Alternatively, the needle can be straight and the surgeon can align the lumen of the needle with the Schlemm's canal by varying the position of the tip of the needle. The needle can be appropriately sized with an outer diameter of 0.015 to 030" and an inner diameter of 0.003" to 0.014". In some embodiments, the delivery device can further have a separate outer tube that exists toward the distal end of the device over the outer diameter of the needle. The outer tube can have an outer diameter of approximately 0.018" to 0.050" and an inner diameter of approximately 0.015" to 0.032". In these embodiments, the needle can be configured to retract within the outer tube and advance out of the outer tube. The outer tube can be constructed of any durable material such as stainless steel, titanium, or any other suitable material. The needle may be constructed of a flexible material such as nitinol such that the needle can have a generally curved shape as described above but can also retract within the outer tube which may be configured as straight. The delivery device can be supplied with the needle retracted within the outer tube and the outer tube can be inserted into the anterior chamber of a patient's eye. Upon entering the anterior chamber, the surgeon can advance the needle out of the outer tube and the needle can return to a curved configuration. The curved needle can then be positioned such that the tip penetrates the inner wall of the Schlemm's canal and the implant can be advanced through the lumen of the needle into the Schlemm's canal. The implant can be marked with varying markings to allow the surgeon to visualize the advancement of the implant through the trabecular meshwork. For example, the implant can have alternating strips of black and white or colored sections which correlate to known distances such as 1 mm such that the surgeon can visualize the circumferential distance they have advanced the implant. Alternatively, a light may be positioned on a section of the implant such as the tip so that the surgeon can further visualize the position of the implant. Alternatively, a separate catheter can be included in the delivery device that is configured to advance through the lumen of the needle and have the implant advanced through its own lumen. The catheter can be comprised of any number of flexible materials such as Pebax or the like. Alternatively, the catheter may be constructed of a rigid tube such as stainless steel that is cut into a pattern, for example a spiral cut pattern using a laser cutting process, that allows the tube to be flexible yet still maintain a strong column strength for advancing through the Schlemm's canal. Additionally, the catheter may have additional materials such as PET (polyester) heat shrink along its outer diameter that may close the spiral openings created by the laser cutting process while still maintaining a degree of flexibility for the catheter. The catheter can be first advanced through the needle into the Schlemm's canal as far as desired by the surgeon, for example 90 to 360 degree around. The catheter may have an inner diameter of approximately 0.002" to 0.012" and an outer diameter of approximately 0.004" to 0.020". Then the implant can be advanced through the lumen of the catheter such that the catheter provides a guide path for the implant. This may be beneficial such that the catheter can be very flexible and inserted through any portion of the Schlemm's canal and then the implant which may be stiffer can be inserted through the catheter. The catheter may then be removed and the implant can be left in place within the Schlemm's canal.

The delivery device may have any number of mechanisms for advancing the implant. A handle may exist that is rigidly connected to the outer tube such that the surgeon may manipulate the position of the handle to orient the outer tube and needle distal tip appropriately. The handle and handle components may be constructed of any number of common medical device materials such as polycarbonate, nylon, or any other suitable materials. The handle may additionally have user interface features which are configured such that the surgeon may control the axial position of the implant or the catheter. For example, a scroll wheel mechanism may exist on the handle of the delivery device where the surgeon rotates the scroll wheel and a component advances or retracts depending on the direction of rotation. The component may be the proximal end of the catheter described above, or the implant, or a separate piece such as an advancing component which is connected at its distal end to the implant or catheter such that as the advancing component advances forward or retracts backwards, the catheter or implant moves with it. The advancing component may be a tube or rod constructed of stainless steel or any other suitable material. The advancing component may be textured or have a rough surface finish such as through bead blasting or laser cutting that allows the roller wheels to effectively engage with it. The proximal end of the handle may include components such as an injection tube and luer so that the surgeon may inject fluids through the injection tube and into the eye. The distal end of the injection tube may be connected to the proximal end of the advancing component, the implant, or the catheter such that fluid communication is provided up to the distal end of the device. The injection tube may be constructed of Pebax or any other suitable tube such that fluid may flow through the lumen of the injection tube. The injection tube may have a size of 0.015" to 0.100" inner diameter and 0.020" to 0.200" outer diameter. The injection tube may be connected to the advancing component, implant, or catheter through any number of methods such as heat shrinking, adhesives, or any other manufacturing method commonly employed by medical device companies.

The scroll wheel may be configured to connect to one or more rolling wheels through axles or gears. The rolling wheels may have compliant materials capable of engaging the implant or catheter or advancing component between the rolling wheels such that the rotation of the scroll wheel causes the rolling wheels to rotate as well, and the advancing component thereby advances or retracts. Alternatively, the scroll wheel may be connected to a pinion gear that engages with a corresponding rack gear. The rack gear may be attached to the implant, the catheter, or an advancing component which is in turn connected to the implant or catheter. The rotation of the pinion gear may cause the rack gear to move axially and advance or retract any connecting components. Alternatively, any number of other advancing mechanisms may be used such as a slider component directly connected to an advancing component.

In at least some embodiments, the force applied by the ocular implant along at least a part of the Schlemm's canal can be a pre-determined force. For example, various features of the implant, such as the size, shape, modulus of elasticity, cross sectional profile and materials, can assist in allowing the ocular implant to assert a desired pre-determined force along at least a part of the wall of the Schlemm's canal in order to increase the flow volume through the Schlemm's canal. Intraocular lenses exist with haptics extending from the lens. The haptics are small pieces of material, typically PMMA (polymethyl methacrylate), polypropylene, PVDF (polyvinylidone fluoride), or the like. The haptics impart a force along the outer wall of the lens capsule to center the lens within the capsule. Measurement of haptic force is typically performed by positioning the lens in a force measurement equipment and compressing the haptics radially and measuring the force (Pärssinen 1997). Typical spring rates for haptics are between 0.5 and 4.0 mN/mm. These forces are generally considered strong enough to impart a force on the lens capsule while not significantly damaging the delicate capsule. Therefore it is desirable for the disclosed ocular implant to have a compressible spring rate of approximately 0.1 mN/mm to 20 mN/mm. Experiments have been conducted by the inventors demonstrating this force is achievable. Round wire comprised of superelastic nitinol of varying diameters were formed into shaped 10 mm rings. When the round wire had a diameter of 0.004" the spring rate was measured at approximately 1.26 mN/mm. Alternatively when the round wire had a diameter of 0.009" the spring rate was measured at approximately 18.02 mN/mm. Additionally varying the predetermined shaped diameter of the ocular implant will change the radial force applied to the Schlemm's canal. In some embodiments the surgeon may choose an ocular implant with a desired predetermined force for a given patient. For example, a certain patient may benefit from only a light radial force while another patient may benefit from a stronger radial force.

In some embodiments, the implant can be made out of a shape memory material which has a larger ring diameter during insertion and can contract into a smaller ring diameter upon implantation and exposure to body temperatures. Alternatively or in addition, the implant can be made out of a shape memory material which has a smaller ring diameter during insertion and can expand into a larger ring diameter upon implantation and exposure to body temperatures. As discussed above, the implant can have a variety of shapes, such as an oscillating and looped configuration. Additionally, the implant can form any one or more of a variety of shapes before and after implantation in order to assist with implantation and increase flow volume through the Schlemm's canal without departing from the scope of this disclosure.

Additionally, some embodiments of the ocular implant can be made out of a nitinol material which can be in a superelastic condition having a known stiffness. In this configuration, as the implant attempts to return to its natural size and shape, such as a ring shape, the implant can impart a radial force on the wall of the Schlemm's canal, including either the outer or inner inside wall of the Schlemm's canal. The radial force on the wall can force the Schlemm's canal to change shape, such as increase the outer diameter or decrease the inner diameter of the Schlemm's canal which can result in an increase in flow volume through the Schlemm's canal. Alternatively other materials may be used which do not exhibit superelastic properties by simple elastic characteristics. For example, stainless steels such as 316 is extremely biocompatible and can exhibit elastic properties with a modulus of approximately 28000 ksi. Other metallic materials include titanium, gold, or any suitable material that is biocompatible and may provide sufficient elasticity and force. Alternatively other non-metallic materials may be used. For example, materials such as PMMA, polypropylene, PVDF and the like are known to provide sufficient force for lens haptics and additionally be biocompatible. Still other materials which are absorbable such as PLA (polylactic acid) or PLGA (polylactic-co-glycolic acid) may be used which impart a radial force for predetermined time period and then dissolve. These absorbable material may further be comprised of other substances such as drugs that are released over time as the absorbable material degrades. Alternatively, other materials may be used such as gels which harden after exposure to elements within the eye. For example, a material may be used which is injected into the Schlemm's canal as a liquid or gel, and then the material may harden such that it contracts or expands to impart a radial force on the Schlemm's canal. Still other embodiments exist where the ocular implant may be comprised of multiple materials. For example, it may be desirable to have one material which imparts a predetermined force such as a nitinol which is coated with a separate material such as Pebax or any other suitable material which may increase ease of insertion through reduced surface tension. Any other suitable combination of any number of other materials. Furthermore, the ocular implant may be coated with a drug or an element containing a drug which releases over a predetermined period. For example, a heparin coating may exist on the outer surface of the implant such that tissue reaction is reduced during implantation.

In addition, the implant material can be made out of a shape memory which can have a shape-set profile, such as the "C" shape, which the implant forms when exposed to its transition temperature which can be set at a pre-determined temperature range, such as above room temperature (approximately 70 degrees Fahrenheit) but below the body temperature (approximately 98 degrees Fahrenheit). In this embodiment, the implant can exist as a malleable ring during implantation but after reaching the body temperature it can return to a superelastic state and impart a radial force onto the Schlemm's canal. Additionally, the implant can be more flexible at a lower temperature such that it can be bent in various ways and form a variety of shapes prior to implantation which can assist with implantation. Alternatively, the transition temperature of the shape memory material can be set at a temperature which is close to the average body temperature of a patient. Body temperatures are known to vary throughout the day and can have a typical range of 2 degrees Fahrenheit. The range of the body temperature may cause the implant to then move back and forth between martensitic and austenitic phases and impart varying forces upon Schlemm's canal. In some patients this may prevent the tissue structures from permanently shifting or moving. The shape memory material may be a metallic composition such as nitinol or a polymer composition such as some polyurethanes with ionic or mesogenic components or any other suitable polymer.

A method of delivering and implanting the ocular implant into the eye is now described. In general, one or more ocular implants can be loaded on a delivery device and implanted to a position within the Schlemm's canal as described herein. The ocular implant can be implanted in the eye via an ab-interno procedure through a limbal incision into the anterior chamber. The ocular implant may be inserted into the Schlemm's canal so that it provides a radial force on the Schlemm's canal and increases the potential for fluid flow through the Schlemm's canal. For example, the surgeon may first assess the appropriate radial force required for a patient and the given diameter of the Schlemm's canal for that patient. The surgeon may then choose an appropriate strength ocular implant which may vary by the wire diameter and circular diameter of the implant. In the case of some embodiments where the ocular is constructed of a shape memory material the surgeon may additionally determine the diurnal temperature range of the patient and further select an appropriate implant which has a transition temperature close to the body temperature of the patient. After selecting the appropriate implant, which may be preloaded into the delivery device, the surgeon can prepare for the procedure. The needle can be positioned on the delivery device such that the distal tip of the needle is constrained by an outer tube with the needle retracted within the outer tube and the ocular implant retracted within the needle. The outer tube can enter the eye through a small corneal incision and access the anterior chamber, such as within the limbus of the cornea. In an embodiment, the incision is very close to the limbus, such as either at the level of the limbus or within 2 mm of the limbus in the clear cornea. The needle can then be advanced out of the outer tube by the surgeon and in some embodiments the needle may have a predefined curve which it assumes once the distal tip is no longer constrained by the outer tube. The needle tip may then be advanced to the trabecular meshwork and likewise the Schlemm's canal such that the needle tip penetrates the wall of Schlemm's canal. The surgeon may choose to move the distal end of the device into an orientation wherein the needle tip is approximately tangential to the Schlemm's canal. The surgeon may then rotate a scroll wheel along the handle of the delivery device that is configured to advance the ocular implant. In some embodiments, a separate advancing component is advanced through the use of roller wheels that engage the advancing component while the distal tip of the advancing component engages with the ocular implant. The ocular implant may be advanced a small amount initially to verify its presence within the Schlemm's canal. Then the ocular implant may be advanced through the lumen of the Schlemm's canal for a circumferential length determined by the length of the ocular implant. During advancement the surgeon may feel the torque required to rotate the scroll wheel and gage whether the implant is correctly within the Schlemm's canal or whether the surgeon should retract and advance again to better position the Schlemm's canal. The advancement of the ocular implant through the Schlemm's canal should typically be smooth and unobstructed. Any number of markings or lines may exist on the implant which may identify to the surgeon the length of insertion of the implant.

In other embodiments a separate catheter may additionally exist within the lumen of the needle and first advanced using a scroll wheel mechanism or other advancing mechanism as described above. The catheter may be flexible enough to easily follow the curve of the Schlemm's canal while simultaneously configured to withstand the necessary column strength necessary for advancing the catheter. In this embodiment, the catheter may be advanced by the surgeon for a desired length approximately equal to the length of the ocular implant. Once the catheter is adequately positioned the ocular implant may then be advanced through the lumen of the catheter. After the ocular implant is in a satisfactory position which may be 180 to 360 degrees around the circumference of the Schlemm's canal, the catheter may then be retracted into the delivery device and the ocular implant may remain in place.

In any number of the embodiments described above, additional methods may exist for the injection of substances into the eye. For example, prior to advancement of the ocular implant visco elastic substances may be injected through the lumen of the needle into the Schlemm's canal and may dilate the Schlemm's canal and may advancement of the ocular implant easier. Alternatively, in some embodiments the ocular implant may be configured as a substantially tubular profile and after implantation into the Schlemm's canal visco elastic or other substances may be injected through the lumen of the ocular implant and through any number of openings existing on the surface of the ocular implant. Still other embodiments exist where a catheter is first advanced into Schlemm's canal to provide a path for the ocular implant. In these embodiments, substances such as visco elastic or saline or any other suitable substance may be injected through the lumen of the catheter either during insertion or upon implantation. The catheter may have a small opening at the distal end of the tube or additional openings may exist along the length of the catheter. In addition any number of other substances which the surgeon desires to inject into the Schlemm's canal, such as heparin or the like, may be injected through the catheter or the lumen of the ocular implant.

In other embodiments the ocular implant described herein may be implanted into various other tissue structures within the eye. For example, capsular tension rings exist which impart a predetermined radial force to the capsular bag of the lens. Certain embodiments of an ocular implant system as disclosed herein may be advantageous to existing devices such as being constructed primarily of nitinol with a phase transition temperature similar to the patient's body temperature such that structures of the eye do not permanently deform or adjust to the force applied by the ocular implant. Still other tissue structures may exist such as the suprachoroidal space which may be suitable for the ocular implant system. For example, it is understood that separation of the sclera and choroid may increase absorption of the aqueous humor by the choroid or other structures. An ocular implant system as disclosed herein may exist as an implant which can be inserted through as small profile opening at the iris root but which may additionally change shapes after implantation and impart a force on the relevant tissue structures such that the sclera and choroid are at least partially separated. This may be advantageous because it may increase absorption of the aqueous humor without the creation of a larger cyclodialysis at the iris root which may cause erratic pressure changes in a patient.

Figure 3A:
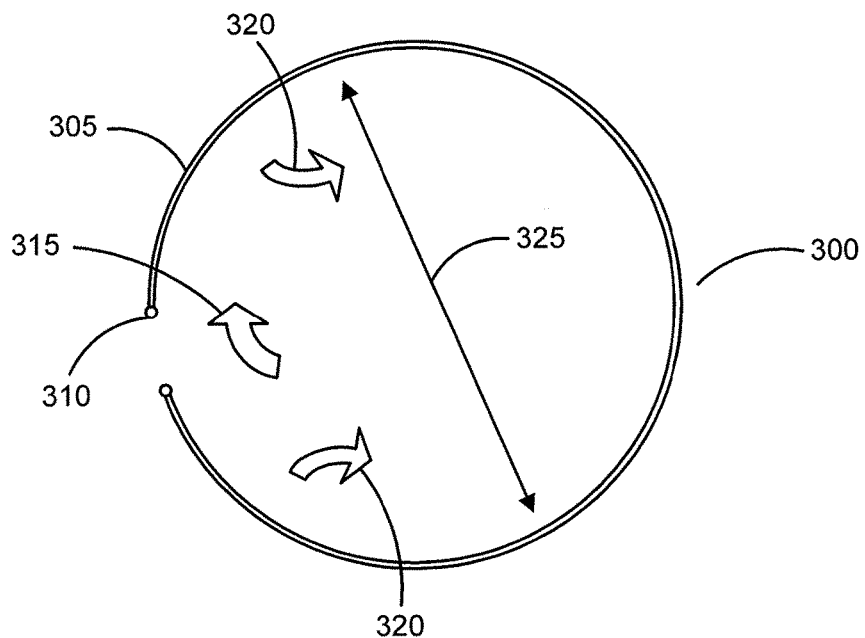
FIG. 3A shows a first embodiment of an ocular implant configured to apply a predetermined inward radial force on at least a part of the inner wall of the Schlemm's canal.

FIG. 3A illustrates an embodiment of an ocular implant 300 configured to apply a radially inward force 320 along at least a part of the inner inside wall of the Schlemm's canal. The radially inward force 320 can assist in forcing the inside wall of the Schlemm's canal to constrict radially which can increase the flow volume through the Schlemm's canal. As shown in FIG. 3A, the ocular implant 300 can have a generally circular ring body 305. In addition, the ocular implant 300 can include rounded tip 310 ends which can form an open angle 315 such that the implant forms a "C" shape, as shown in FIG. 3A. In addition, the size of the open angle 315 can vary depending on how much the ring body 305 either expands or contracts. As discussed above, the ocular implant 300 can have any of a variety of shapes and sizes, and can be made out of any number of a variety of materials, including at least those described herein.

Figure 3B:
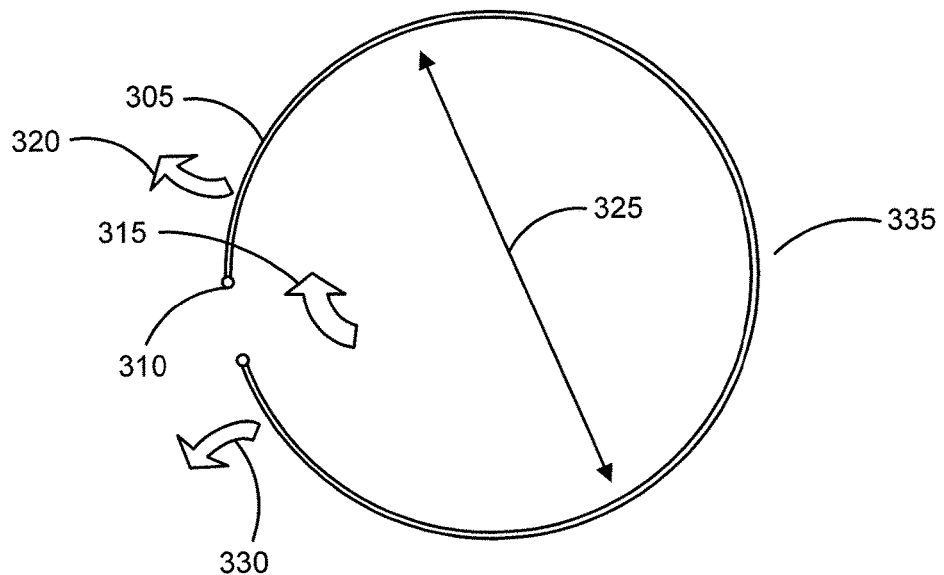
FIG. 3B shows another embodiment of an ocular implant configured to apply a predetermined outward radial force on at least a part of the outer wall of the Schlemm's canal.

FIG. 3B illustrates an embodiment of an ocular implant 335 configured to apply a radially outward force 330 along at least a part of the outer wall of the Schlemm's canal. The radially outward force 330 can assist in forcing the outside diameter of the Schlemm's canal to expand radially which can increase the flow volume through the Schlemm's canal. As shown in FIG. 3B, the ocular implant 335 can have a generally circular ring body 305. In addition, the ocular implant 335 can include rounded tip 310 ends which can form an open angle 315 such that the implant forms a "C" shape, as shown in FIG. 3B. In addition, the size of the open angle 315 can vary depending on how much the ring body 305 either expands or contracts. As discussed above, the ocular implant 335 can have any of a variety of shapes and sizes, and can be made out of any number of a variety of materials, including at least those described herein.

Figure 3C:
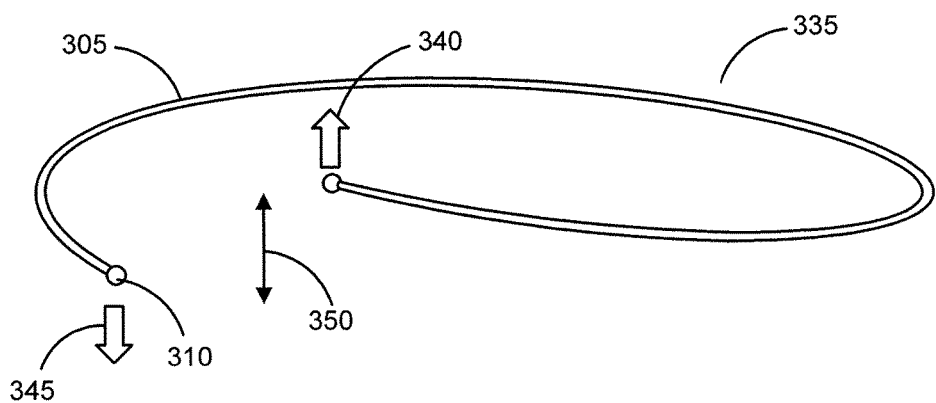
FIG. 3C shows another embodiment of an ocular implant configured to apply a predetermined upward force and downward force on a least a part of the wall of the Schlemm's canal.

FIG. 3C illustrates an embodiment of an ocular implant 355 configured to apply an additional upward force 340 and downward force 345 along at least a part of the upper and lower walls of the Schlemm's canal. The upward force 340 and downward force 345 can assist the cross-sectional diameter of the Schlemm's canal to expand which can increase the flow volume through the Schlemm's canal. As shown in FIG. 3C, the ocular implant 355 can have a generally circular ring body 305. In addition, the ocular implant 355 can have a vertical separation 350 between the two rounded tips 310 such that when the rounded tips 310 are constricted by a tissue structure such as Schlemm's canal they impart an upward force 340 and downward force 345, as shown in FIG. 3B. The size of the vertical separation 350 can vary depending on how much the force is desired to impart upon the Schlemm's canal. As discussed above, the ocular implant 355 can have any of a variety of shapes and sizes, and can be made out of any number of a variety of materials, including at least those described herein.

Figure 4A:
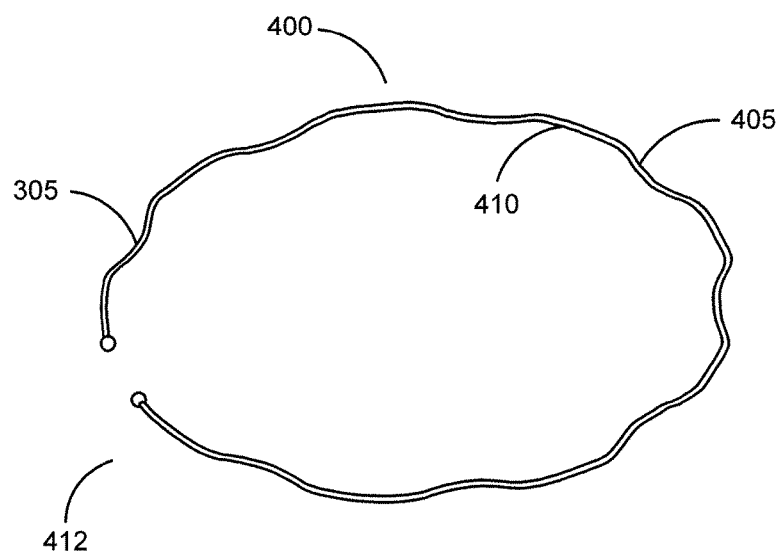
FIG. 4A shows another embodiment of a ocular implant having an oscillating shape which can impart both a predetermined inward and outward force along the inner and outer wall of the Schlemm's canal, respectively.

FIG. 4A illustrates an embodiment of an ocular implant 400 having an oscillating shape 412 which can be configured to apply a radially outward force 330 along an outer wall 405 of the implant 400 and a radially inward force 420 along an inner wall 410 of the implant along at least a part of the outer and inner inside wall of the Schlemm's canal, respectively. The radially outward force 330 can assist in forcing the outside diameter of the Schlemm's canal to expand radially and the radially inward force 320 can assist in forcing the inner diameter of the Schlemm's canal to constrict radially which can increase the flow volume through the Schlemm's canal. As shown in FIG. 4A, the ocular implant 400 can have a generally circular ring body 305 including at least one oscillation along the length of the circular ring body 305. In addition, the ocular implant 400 can include rounded tip 310 ends which can form an open angle 315 such that the implant forms a "C" shape, as shown in FIG. 4A. In addition, the size of the open angle 315 can vary depending on how much the ring body 305 either expands or contracts. As discussed above, the ocular implant 400 can have any of a variety of shapes and sizes, and can be made out of any number of a variety of materials, including at least those described herein.

Figure 4B:
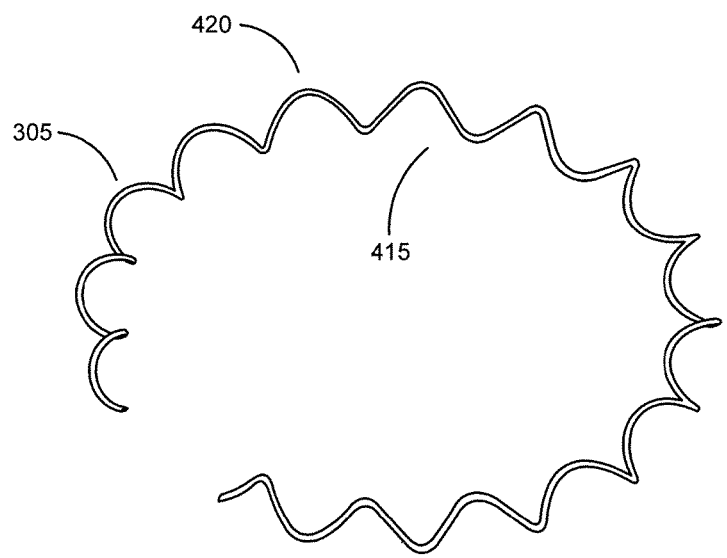
FIG. 4B shows another embodiment of a ocular implant having a looped shape which can impart a predetermined force along at least the inner and outer wall of the Schlemm's canal.

FIG. 4B illustrates an embodiment of an ocular implant 420 having a looped shape 415 which can be configured to apply a radial force along any part of the inside wall of the Schlemm's canal. The looped shape 415 can allow the ocular implant 420 to contact a variety of positions along the inside wall of the Schlemm's canal which can allow the implant 420 to apply a force along a variety of positions along the inside wall. For example, expansion of the ocular implant 420 can allow the ocular implant 420 to expand the diameter of the Schlemm's canal in more than one direction which can increase the flow volume through the Schlemm's canal. As shown in FIG. 4B, the ocular implant 420 can have a generally circular ring body 305 including coiled loops along the length of the circular ring body 305. In addition, the ocular implant 420 can include rounded tip 310 ends which can form an open angle 315 such that the implant forms a "C" shape, as shown in FIG. 4B. In addition, the size of the open angle 315 can vary depending on how much the ring body 305 either expands or contracts. As discussed above, the ocular implant 420 can have any of a variety of shapes and sizes, and can be made out of any number of a variety of materials, including at least those described herein.

Figure 4C:
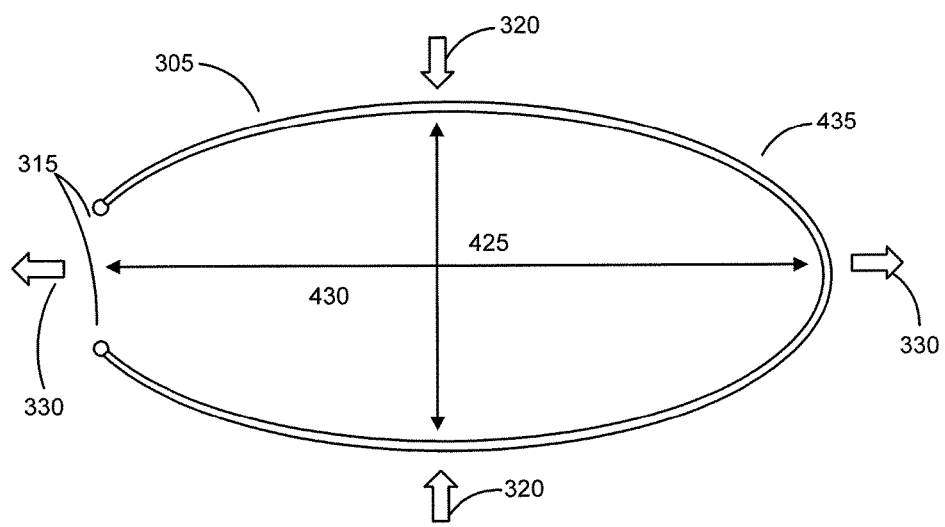
FIG. 4C shows another embodiment of an ocular implant having an oval shape which can impart a predetermined force along at least the inner and outer wall of the Schlemm's canal.

FIG. 4C illustrates an embodiment of an ocular implant 435 having an oval shape which can be configured to apply a radial force along any part of the inside and outside wall of the Schlemm's canal. The oval shape can allow the ocular implant 435 to contact a variety of positions along the inside wall of the Schlemm's canal which can allow the implant 435 to apply a force along a variety of positions along the inside and outside wall. For example, ocular implant 435 can have a minor axis 425 which is approximately less than the diameter of the Schlemm's canal and a major axis 430 which is approximately larger than the diameter of the Schlemm's canal. As the ocular implant 435 is constrained by the diameter of the Schlemm's canal, the portion of the ocular implant close to the minor axis 425 can impart a generally inward force 320 onto the Schlemm's canal inner wall. Likewise the portion of the ocular implant 435 close to the major axis 430 can impart a generally outward force 330 onto the Schlemm's canal. In addition, the ocular implant 435 can include rounded tip 310 ends which can form an open angle 315 such that the implant forms a "C" shape, as shown in FIG. 4C. In addition, the size of the open angle 315 can vary depending on how much the ring body 305 either expands or contracts. As discussed above, the ocular implant 435 can have any of a variety of shapes and sizes, and can be made out of any number of a variety of materials, including at least those described herein.

Figure 5A:
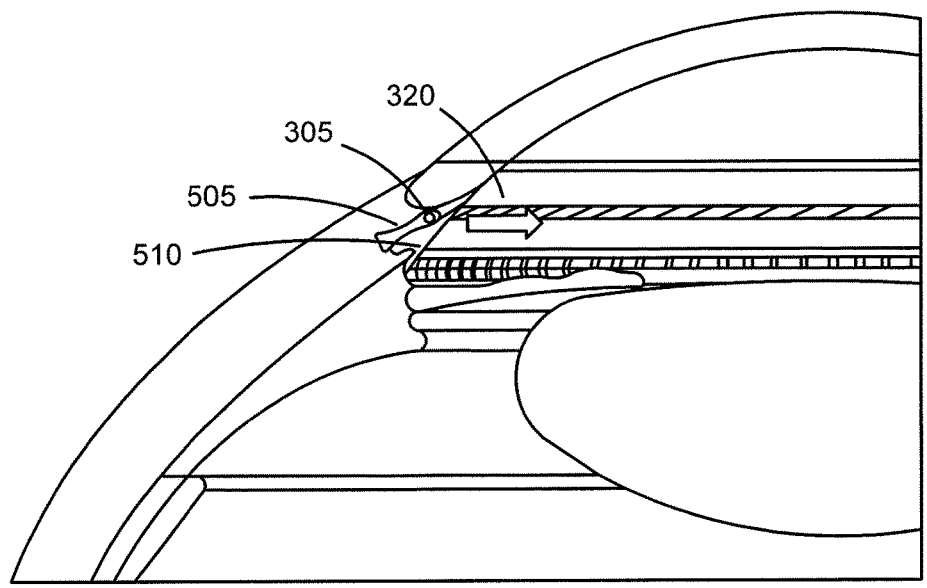
FIG. 5A shows a side cross section view of an embodiment of the ocular implant implanted in the Schlemm's Canal of an eye.
Figure 5B:
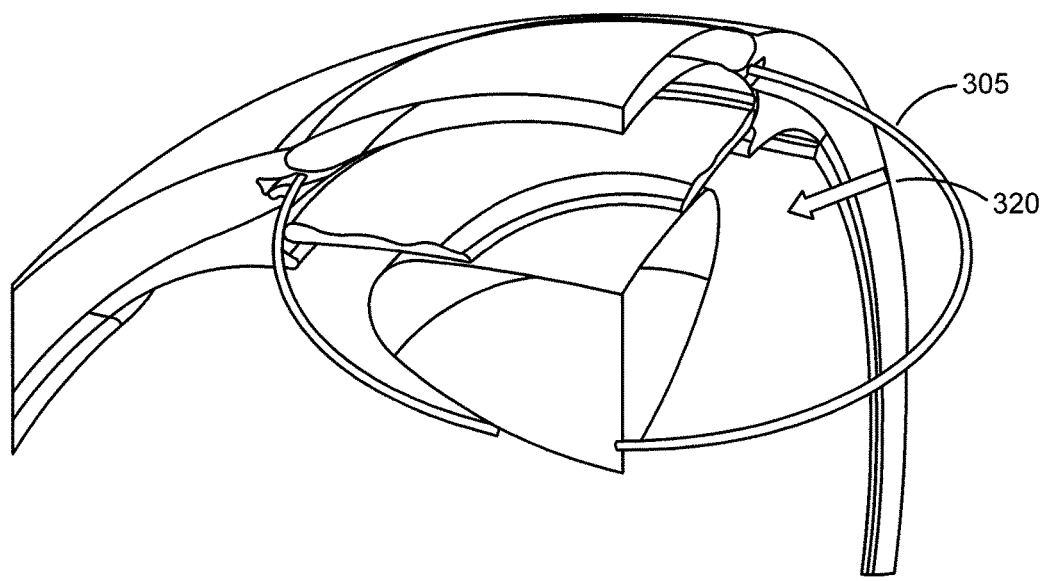
FIG. 5B shows a perspective cross section view of an embodiment of the ocular implant implanted in the Schlemm's Canal of an eye.

FIGS. 5A and 5B illustrate an ocular implant, such as the ocular implant 300 shown in FIG. 3A, implanted in the Schlemm's canal. The ocular implant 300 in FIGS. 5A and 5B is shown as applying an inward force 320 along the inside wall of the Schlemm's canal resulting in a decrease in the inner diameter of the Schlemm's canal and an increase in the flow volume through the Schlemm's canal. As discussed above, the ocular implant 300 can be placed into the Schlemm's canal via an ab-interno procedure. For example, a surgeon can use a delivery device to access the Schlemm's canal and the implant 300 can be inserted through the needle of a delivery device into the Schlemm's canal. Once the implant 300 has been placed into the Schlemm's canal, the implant 300 can change shape, such as contract or expand, in order to impart a radial force 320 onto at least a part of the inside wall of the Schlemm's canal. This can increase the diameter of the flow pathway in the Schlemm's canal which can increase the flow volume through the Schlemm's canal. Therefore, an increase in flow volume, such as aqueous fluid, through the Schlemm's canal can assist with decreasing the inner ocular pressure in an eye, such as an eye suffering from glaucoma.

Figure 6A:
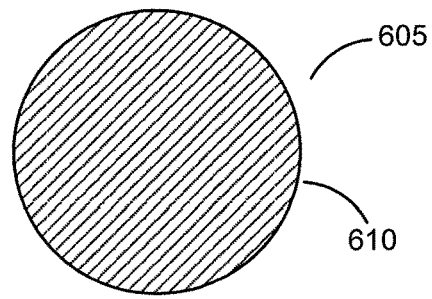
FIG. 6A shows a cross-sectional profile of a solid wire ocular implant.
Figure 6B:
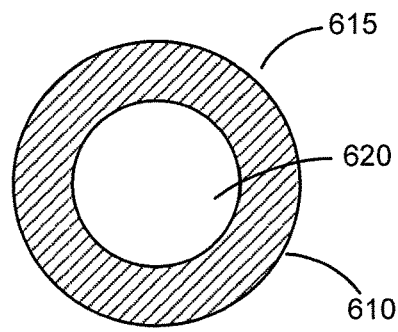
FIG. 6B shows a cross-sectional profile of a tubular ocular implant.

FIGS. 6A and 6B illustrate a variety of cross-sectional profiles the ocular implant 300 may have at various locations along its circumference. In FIG. 6A a solid round cross-sectional profile 605 is shown with an outer diameter 610. This may be constructed from a single round wire of material such as the materials discussed above. In FIG. 6B a tubular cross-sectional profile 615 is shown. In this embodiment, the ocular implant may be constructed of a tube of material which is formed into a generally ring shaped body. Additionally, multiple materials may be used in such constructions such as lamination layers on the outer diameter or core wires at the inner diameter 620 of any number of materials as disclosed herein. As discussed above, the ocular implant 300 can have any of a variety of shapes and sizes, and can be made out of any number of a variety of materials, including at least those described herein.

Figure 6C:
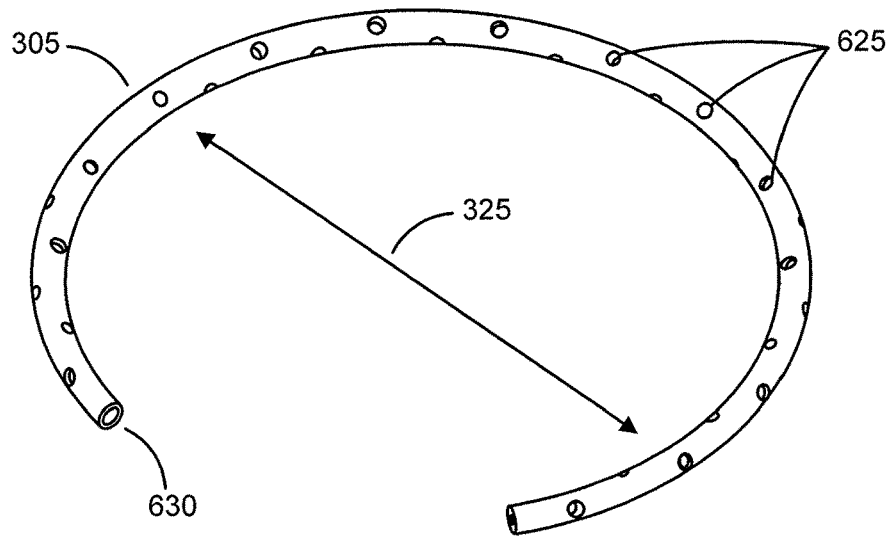
FIG. 6C shows a tubular ocular implant with multiple openings configured for fluid communication between the lumen of the ocular implant and the Schlemm's canal.

FIG. 6C illustrates an ocular implant with a substantially tubular cross-sectional profile 615. Additionally, the ocular implant has multiple openings 625 which create fluid communication between the inner lumen 630 of the ocular implant with the outer surface. The inner lumen 630 is shown to extend through the two rounded ends of the implant.

Figure 7A:
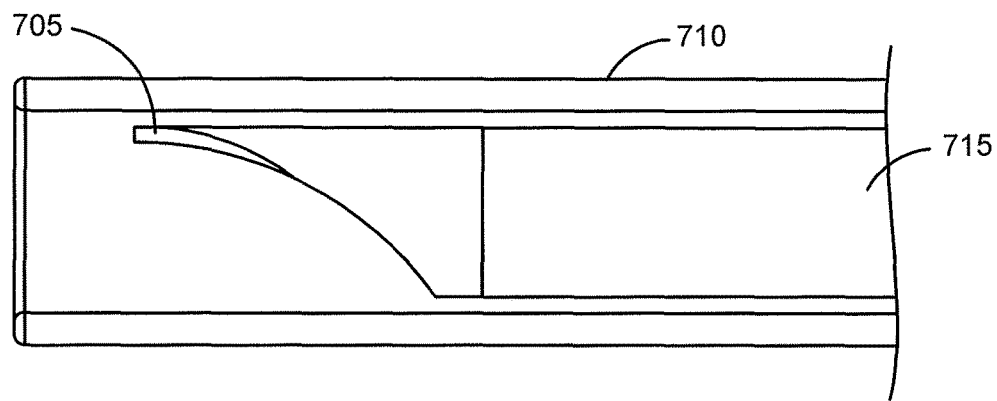
FIG. 7A shows a configuration of a distal end of a delivery device with a needle retracted within an outer tube.
Figure 7B:
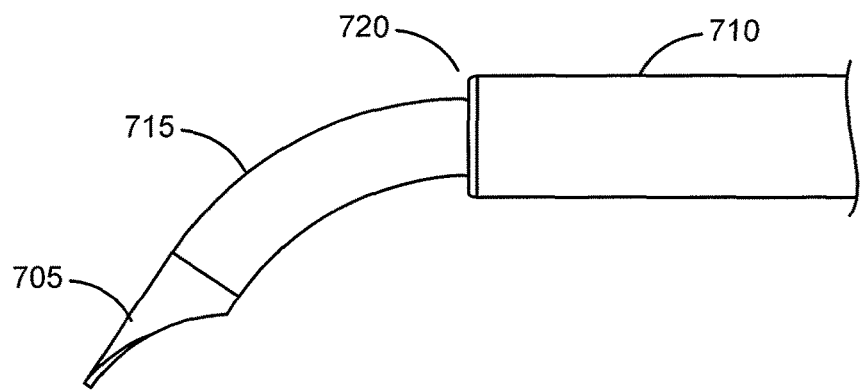
FIG. 7B shows a configuration of a distal end of a delivery device with a needle with a curved section advanced out of an outer tube.
Figure 7C:
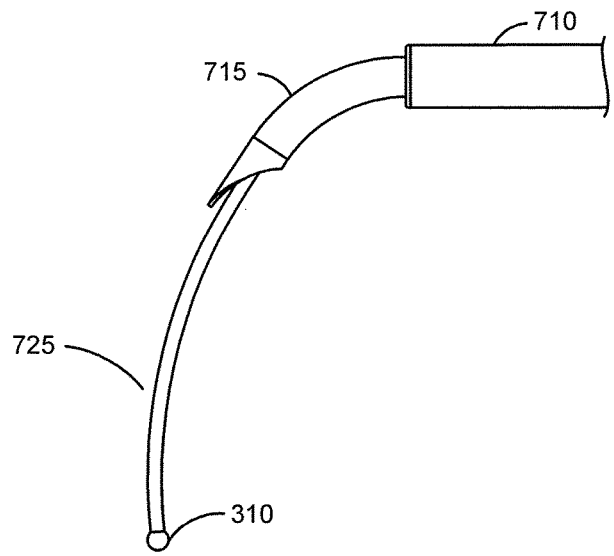
FIG. 7C shows a configuration of a distal end of a delivery device with a needle with a curved section advanced out of an outer tube and an ocular implant advanced out of the needle.

FIGS. 7A, 7B, and 7C illustrate a distal end of a delivery device. An outer tube 710 exists which is a generally straight tube with a rounded tip. The needle 715 is concentric with the outer tube 710 and may advance in and out of the outer tube 710. In FIG. 7A the distal tip of the needle 705 is shown to be retracted within the outer tube 710 such as would be useful during insertion of the delivery device into the eye. In FIG. 7B the needle 715 is shown advanced out of the outer tube 710. Additionally, a curved section 720 on the needle 715 exists which changes the direction of the lumen of the needle 715. The curved section 720 of the needle 715 may be predetermined by a bend in the needle 715 that is constrained to be straight when retracted within the outer tube 710. The lumen of the needle 715 may be positioned such that it is substantially tangential to the Schlemm's canal and the distal tip of the needle 715 may penetrate the inner wall of the Schlemm's canal. In FIG. 7C the ocular implant 725 is shown advancing from the lumen of the needle 715. The ocular implant 725 may be advanced for the entire length of the ocular implant 725 such that it is inserted into the Schlemm's canal partially or fully.

Figure 8:
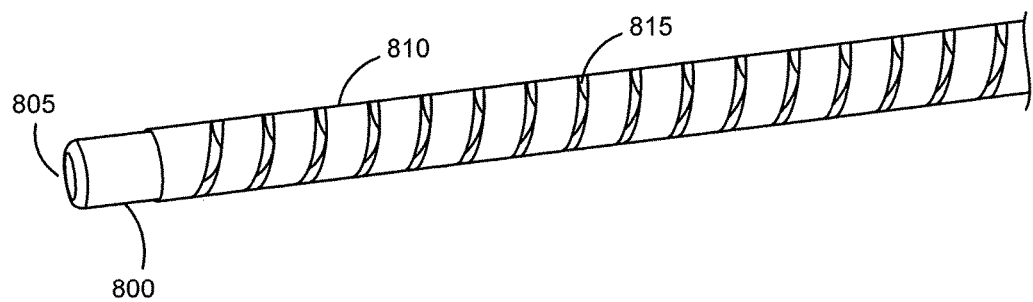
FIG. 8 shows an embodiment of a catheter configured with a laser cut pattern and a catheter sheath.

FIG. 8 illustrates an embodiment of the delivery device which includes a catheter 800. The catheter 800 may be constructed from any number of materials and shapes as disclosed herein. For example, the catheter 800 is shown in FIG. 8 with a laser cut pattern 815 which exists as a spiral cut along the length of the catheter 800. The laser cut pattern 815 allows the catheter 800 to be constructed from an otherwise rigid material such as stainless steel but additionally be flexible as bends can easily take place along the length of the laser cut pattern. Additionally a catheter sheath 810 is shown along at least a portion of the catheter 800. The catheter sheath 810 may cover at least some of the laser cut pattern 815 such that substances injected through the lumen of the catheter 800 continue through the lumen of the catheter all the way to the distal lumen 805 of the catheter 800. A rounded tip or any other profile of tip exists at the end of the catheter 800. The catheter 800 may exist concentrically within the lumen of the needle 715 and the ocular implant 725 may exist concentrically within the lumen of the catheter 800. The catheter 800 may be first advanced from the lumen of the needle 715 once the distal tip of the needle 715 has penetrated the Schlemm's canal such that as the catheter 800 advances it enters the Schlemm's canal. The catheter 800 may advance through the Schlemm's canal for any desired circumferential length. The ocular implant 725 may then be advanced through the lumen of the catheter 800 until it is fully or partially within the Schlemm's canal. The catheter 800 may then be retracted such that the ocular implant 725 remains within the Schlemm's canal at the appropriate location. Substances or fluids may be additionally injected through the lumen of the catheter 800 or the ocular implant 725 at any point during the procedure.

Figure 9A:
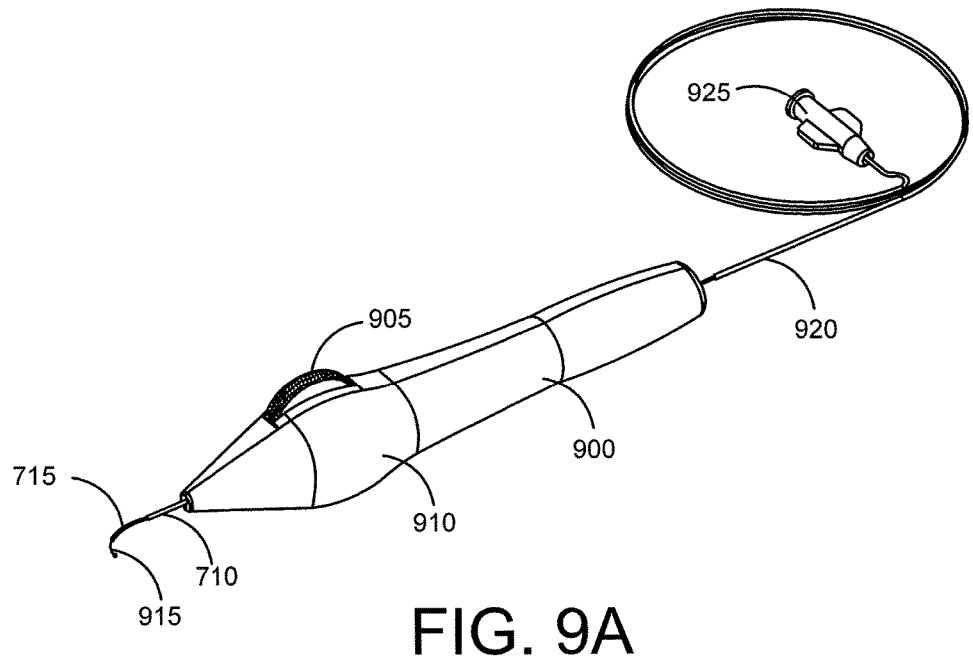
FIG. 9A shows an embodiment of a delivery device with a scroll wheel mechanism and components necessary for injection of substances in the eye.
Figure 9B:
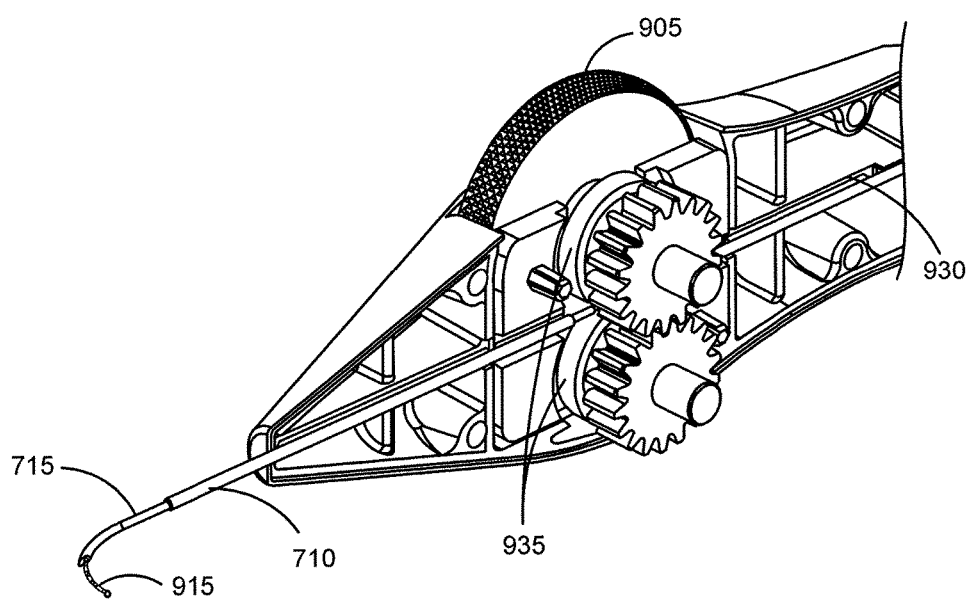
FIG. 9B shows more detail of the inner components of an embodiment of a delivery device with a scroll wheel mechanism.
Figure 9C:
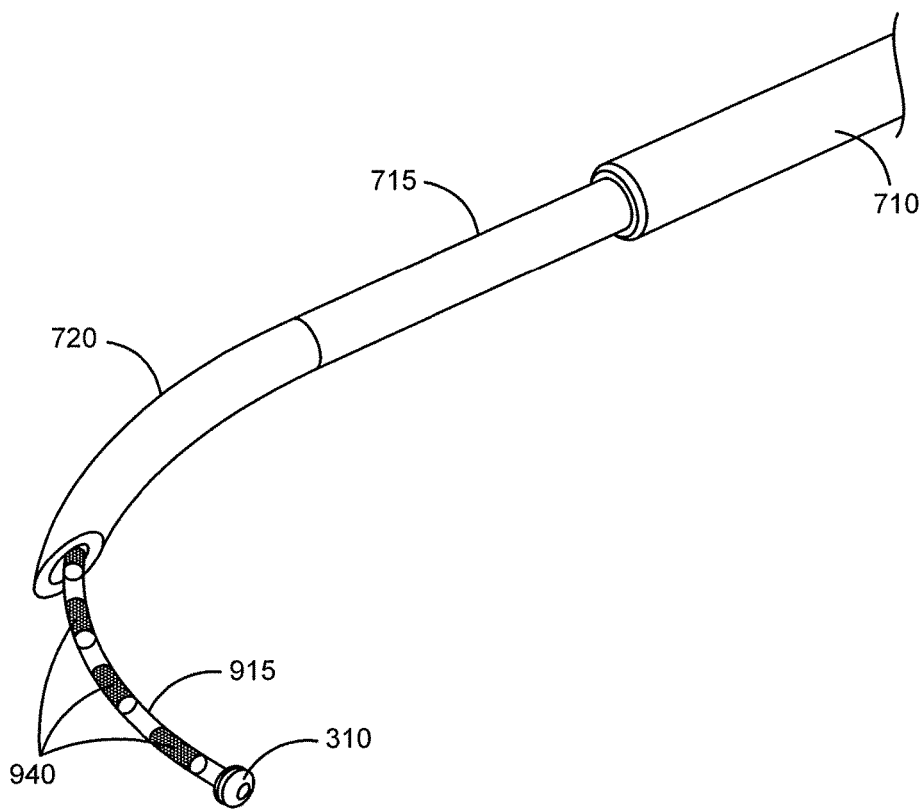
FIG. 9C shows more detail of the distal end of an embodiment of a delivery device with a scroll wheel mechanism and an ocular implant with laser markings for depth indication.

In FIGS. 9A, 9B, and 9C illustrate an embodiment of a delivery device 900 utilizing a scroll wheel 905 mechanism. In FIG. 9A the delivery device 900 is shown with a handle 910 which the surgeon may manipulate and control from outside the eye. The delivery device 900 is shown with a scroll wheel 905 along the top of the handle 910 which the surgeon may rotate in either a clockwise or counter-clockwise direction to advance or retract a component within the handle 910 of the delivery device 900. At the proximal end of the delivery device 900 a luer 925 and injection tube 920 are shown which may provide fluid communication from the luer 925 to any number of components at the distal end of the delivery device 900. For example, in some embodiments where a catheter 800 is used, the injection tube 920 may be connected to the proximal end of the catheter 800 such that the surgeon may inject substances into the luer 925 and those substances may subsequently be injected through the lumen of the catheter 800 and into the eye. In FIG. 9B the delivery device 900 is shown in greater detail with one half of the handle 910 removed for illustration of the inner components of the delivery device 900. Two rolling wheels 935 are shown with the top rolling wheel 935 connected directly to the scroll wheel 905 and the bottom roller wheel 935 engaged with a set of gears which transmit torque from the scroll wheel 905 to the bottom roller wheel 935. As the scroll wheel 905 rotates, the roller wheels 935 rotate in opposing directions. The roller wheels 935 may be constructed from a compliant material that is capable of engaging with an advancing component 930. The advancing component 930 may exist as shown between the rolling wheels 935 such that as the rolling wheels 935 rotate, the advancing component 930 moves axially forward or backward. The advancing component 930 may be connected at its distal end to the implant 915 or catheter 800. Alternatively, as disclosed herein other embodiments exist where there is no advancing component 930 and the roller wheels 935 are directly engaged with the implant 915 or the catheter 800. In FIG. 9C the distal end of the delivery device 900 is shown in greater detail. The ocular implant 915 is shown advanced out of the needle 715 which is in turn advanced out of the outer tube 710. The ocular implant 915 is shown with multiple length markings 940 which may identify to the surgeon the circumferential length they have delivery the ocular implant 915. Alternatively, in some embodiments where a catheter 800 exists in addition to the ocular implant 915, the length markings 940 may exist on the catheter 800.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An ocular implant for implanting in the Schlemm's canal in an eye comprising:
   an implant having a ring shaped body formed of only a single strand and being sized and shaped to be positioned inside the Schlemm's canal, the ring shaped body being configured to apply a pre-determined radial force along at least a part of a wall of the Schlemm's canal so as to change the shape of the Schlemm's canal and allow an increase in flow volume through the Schlemm's canal and wherein the ring shaped body has an outermost periphery that forms an oval, wherein the oval defines an outermost shape of the entire ring shaped body, the oval defined by a minor axis less than the diameter of the Schlemm's canal and a major axis larger than the diameter of the Schlemm's canal, and wherein a single, oval-shaped lumen extends continuously through the entire ring shaped body;
   wherein the ring shaped body has two discrete ends which are disconnected and overlapping.

2. The ocular implant of claim 1 wherein at least one of the discrete ends of the implant is configured to remain within the anterior chamber of the eye after implantation.

3. The ocular implant of claim 1 wherein at least one of the discrete ends of the implant is substantially rounded.

4. The ocular implant of claim 1 wherein the ring shaped body is configured to impart a radial force upon implantation onto an inward wall of Schlemm's canal.

5. The ocular implant of claim 1 wherein the ring shaped body is configured to impart a radial force upon implantation onto an outward wall of Schlemm's canal.

6. The ocular implant of claim 1 wherein the ring shaped body is configured to impart a radial force upon implantation onto both an inward and an outward wall of Schlemm's canal.

7. The ocular implant of claim 1 wherein the ring shaped body is further configured to impart a vertical force on an upper and lower wall of Schlemm's canal.

8. The ocular implant of claim 1 wherein the shape of the ring shaped body is substantially ovular.

9. The ocular implant of claim 1 wherein the ring shaped body includes at least one oscillation along its length.

10. The ocular implant of claim 9 wherein at least one oscillation is a coiled loop.

11. The ocular implant of claim 1 wherein the ring shaped body comprises a medical grade material.

12. The ocular implant of claim 11 wherein the medical grade material includes a shape memory material comprising at least one of nitinol and a shape memory polymer.

13. The ocular implant of claim 12 wherein the shape memory material has a transition temperature below body temperature.

14. The ocular implant of claim 12 wherein the shape memory material has a transition temperature close to a patient's body temperature.

15. The ocular implant of claim 13 wherein daily variations in body temperature apply variable forces to the Schlemm's canal.

16. The ocular implant of claim 11 wherein the medical grade material includes elastically deformable materials comprising at least one of stainless steel and titanium.

17. The ocular implant of claim 1 wherein a cross-sectional profile of the ring shaped body is substantially tubular.

18. The ocular implant of claim 17 wherein the ring shaped body has openings along a circumference the ring shaped body whereby the inner lumen is in fluid communication with an outer surface of the implant.

19. The ocular implant of claim 17 wherein the ring shaped body is configured such that substances may be injected through the lumen of the implant.

20. The ocular implant of claim 1 wherein the cross-sectional profile of the ring shaped body is variable along a circumference of the implant.

21. The ocular implant of claim 1, wherein the oval being entirely positioned in a flat plane.

* * * * *